US00PP29022P3

(12) United States Plant Patent
Hoogkamp

(10) Patent No.: US PP29,022 P3
(45) Date of Patent: Feb. 27, 2018

(54) ***SPATHIPHYLLUM* PLANT NAMED 'SPAMOBLA'**

(50) Latin Name: ***Spathiphyllum* Schott**
Varietal Denomination: Spamobla

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 25 days.

(21) Appl. No.: 14/999,693

(22) Filed: Jun. 16, 2016

(65) Prior Publication Data

US 2017/0367242 P1 Dec. 21, 2017

(51) Int. Cl.
*A01H 5/02* (2006.01)

(52) U.S. Cl.
USPC ..... Plt./364

(58) Field of Classification Search
USPC ..... Plt./364
See application file for complete search history.

(56) References Cited

PUBLICATIONS

UPOV hit on *Spathiphyllum* plant named 'Spamobla', QZ PBR 20160985, Apr. 21, 2016.*

* cited by examiner

*Primary Examiner* — Anne M Grunberg
(74) *Attorney, Agent, or Firm* — C. A. Whealy

(57) ABSTRACT

A new and distinct cultivar of *Spathiphyllum* plant named 'Spamobla', characterized by its upright, outwardly arching and uniform plant habit; freely clumping growth habit; bushy and dense plants; glossy dark green-colored leaves; freely flowering habit; large creamy white-colored spathes that are positioned above and between the foliar plane on strong and erect scapes; and good inflorescence longevity.

2 Drawing Sheets

Botanical designation: *Spathiphyllum* Schott.
Cultivar denomination: 'SPAMOBLA'.

BACKGROUND OF THE INVENTION

The present invention relates to a new and distinct cultivar of *Spathiphyllum* plant, botanically known as *Spathiphyllum* Schott. and hereinafter referred to by the cultivar name 'Spamobla'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in August, 2011 of a proprietary selection of *Spathiphyllum* Schott. identified as code number 20092316-39, not patented, as the female, or seed, parent with a proprietary selection of *Spathiphyllum* Schott. identified as code number 20111206-01, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in December, 2012.

Asexual reproduction of the new *Spathiphyllum* plant by tissue culture in a controlled environment in Naaldwijk, The Netherlands since December, 2012 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamobla'. These characteristics in combination distinguish 'Spamobla' as a new and distinct *Spathiphyllum* plant:

1. Upright, outwardly arching and uniform plant habit.
2. Freely clumping growth habit; bushy and dense plants.
3. Glossy dark green-colored leaves.
4. Freely flowering habit.
5. Large creamy white-colored spathes that are positioned above and between the foliar plane on strong and erect scapes.
6. Good inflorescence longevity.

Plants of the new *Spathiphyllum* differ from plants of the female parent selection in the following characteristics:

1. Leaves of plants of the new *Spathiphyllum* are darker green in color than leaves of plants of the female parent selection.
2. Scapes of plants of the new *Spathiphyllum* are longer than scapes of plants of the female parent selection.

Plants of the new *Spathiphyllum* differ from plants of the male parent selection in the following characteristics:

1. Leaves of plants of the new *Spathiphyllum* are darker green in color than leaves of plants of the male parent selection.

2. Scapes of plants of the new *Spathiphyllum* are longer than scapes of plants of the male parent selection.

Plants of the new *Spathiphyllum* can also be compared to plants of *Spathiphyllum* Schott. 'Sparanke', disclosed in U.S. Plant Pat. No. 21,294. In side-by-side comparisons conducted in Naaldwijk, The Netherlands, plants of the new *Spathiphyllum* differed from plants of 'Sparanke' in the following characteristics:

1. Plants of the new *Spathiphyllum* were more freely clumping and bushier than plants of 'Sparanke'.
2. Leaves of plants of the new *Spathiphyllum* were broader than leaves of plants of 'Sparanke'.
3. Scapes of plants of the new *Spathiphyllum* were shorter than scapes of plants of 'Sparanke'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spamobla' grown in a container.

The photograph on the second sheet is a close-up view of a typical inflorescence of 'Spamobla'.

DETAILED BOTANICAL DESCRIPTION

The aforementioned photographs and following observations and measurements describe plants grown during the spring in 14-cm containers in a glass-covered greenhouse in Naaldwijk, The Netherlands and under cultural practices typical of commercial *Spathiphyllum* production. During the production of the plants, day temperatures ranged from 20° C. to 24° C., night temperatures ranged from 19° C. to 21° C. and light levels averaged 5 klux. Plants were 37 weeks old when the photographs and the detailed description were taken. In the following description, color references are made to The Royal Horticultural Society Colour Chart, 2015 Edition, except where general terms of ordinary dictionary significance are used.

Botanical classification: *Spathiphyllum* Schott. 'Spamobla'.

Parentage:

*Female, or seed, parent*.—Proprietary selection of *Spathiphyllum* Schott. identified as code number 20092316-39, not patented.

*Male, or pollen, parent*.—Proprietary selection of *Spathiphyllum* Schott. identified as code number 20111206-01, not patented.

Propagation:

*Type*.—By tissue culture.

*Time to initiate roots, summer and winter*.—About eleven days at temperatures about 23° C.

*Time to produce a rooted young plant, summer*.—About 215 days at temperatures about 21° C.

*Time to produce a rooted young plant, winter*.—About 240 days at temperatures about 21° C.

*Root description*.—Medium in thickness, fibrous; white in color.

*Rooting habit*.—Moderately branching, medium density.

Plant description:

*Plant and growth habit*.—Upright and outwardly arching plant habit; overall plant shape, broadly inverted triangle; moderately vigorous growth habit; moderate growth rate.

*Clumping habit*.—Freely clumping habit, bushy and dense growth habit; about 14 clumps develop per plant.

*Plant height, from soil level to top of leaf plane*.—About 37 cm.

*Plant height, from soil level to top of inflorescences*.—About 56.5 cm.

*Plant diameter or spread*.—About 57.8 cm.

*Leaf description*.—Arrangement: Alternate; simple. Length: About 22 cm. Width: About 8 cm. Shape: Narrowly ovate to narrowly elliptic. Apex: Narrow and long apiculate. Base: Attenuate. Margin: Entire; moderately undulate. Texture and luster, upper and lower surfaces: Smooth, glabrous; glossy. Venation pattern: Pinnate. Color: Developing leaves, upper surface: Darker than between 141A and 143A. Developing leaves, lower surface: Close to 137C. Fully expanded leaves, upper surface: Close to between 139A and N189A; venation, slightly darker than 143A. Fully expanded leaves, lower surface: Close to 147A; venation, close to 144A to 144B. Petioles: Length (excluding geniculum): About 12.7 cm. Diameter, just below geniculum: About 3 mm. Diameter, at plant base: About 7 mm. Texture and luster, upper and lower surfaces: Smooth, glabrous; slightly glossy. Color, upper surface: Slightly darker than between 141B and 143A. Color, lower surface: Close to 143B. Geniculum length: About 3 cm. Geniculum diameter: About 4 mm. Geniculum texture and luster, upper and lower surfaces: Smooth, glabrous; slightly glossy. Geniculum color, upper and lower surfaces: Close to 144B. Wing length: About 13.4 cm. Wing diameter: About 5 mm. Wing color: Close to 144A.

Inflorescence description:

*Inflorescence arrangement and flowering habit*.—Moderately to strongly cupped erect spathes with columnar spadices held above and between the foliar plane on strong and erect scapes; flowering structures arise from leaf axils; plants begin flowering about five months after planting; freely and continuous flowering year-round under greenhouse conditions in The Netherlands; freely flowering habit, typically about twelve inflorescences develop per plant.

*Fragrance*.—Faintly to moderately fragrant; fragrance, sweet and pleasant.

*Inflorescence longevity*.—Inflorescences last more than three weeks on the plant; inflorescences persistent.

*Spathe*.—Length: About 14.9 cm. Width: About 6.5 cm. Depth: About 4.4 cm. Shape: Ovate; twisting and curling towards the apex. Apex: Apiculate; twisting and curled. Base: Attenuate. Margin: Entire; slightly undulate. Texture and luster, front surface: Smooth, glabrous; slightly leathery; slightly to moderately glossy. Texture and luster, rear surface: Smooth, glabrous; slightly leathery; glossy. Color: When developing, front surface: Close to 150D; towards the apex, close to 141A; main vein, close to 143B. When developing, rear surface: Close to 150D; towards the apex and main vein, close to 143A. Fully developed, front surface: Close to between 150D, 155A and 157A; towards the apex, close to 143A; main vein, close to 194D; with development, color becoming closer to 145B. Fully developed, rear surface: Close to between 150D and 155A; towards the apex and main vein, close to 143A; with development, color becoming closer to 145B.

*Spadix*.—Length: About 4.9 cm. Diameter: About 1.4 cm. Shape: Columnar, tapering towards the apex; apex, obtuse; base, obtuse; cross-section, rounded. Aspect: Close to erect, about 20° from scape axis. Color, immature: Close to between 155A and 157D. Color, mature: Close to 158D. Flowers: Quantity per spadix: Numerous, about 150. Shape: Rounded. Height: About 3 mm. Diameter: About 4 mm. Anther color: Close to 158A. Pollen amount: Scarce. Pollen color: Close to 155D. Stigma color: Close to 158D. Ovary color: Close to 158D.

*Scapes*.—Length: About 34.9 cm. Diameter: About 4.5 mm. Strength: Strong. Aspect: Erect. Texture and luster: Smooth, glabrous; moderately glossy. Color: Slightly darker than 143C.

*Seeds and fruits*.—Seed and fruit development have not been observed on plants of the new *Spathiphyllum*.

Disease & pest resistance: Plants of the new *Spathiphyllum* have not been observed to be resistant to pathogens or pests common to *Spathiphyllum* plants.

Temperature tolerance: Plants of the new *Spathiphyllum* have been observed to be tolerant to high temperatures about 40° C. and to be suitable for USDA Hardiness Zones 10 to 13.

It is claimed:

1. A new and distinct *Spathiphyllum* plant named 'Spamobla' as illustrated and described.

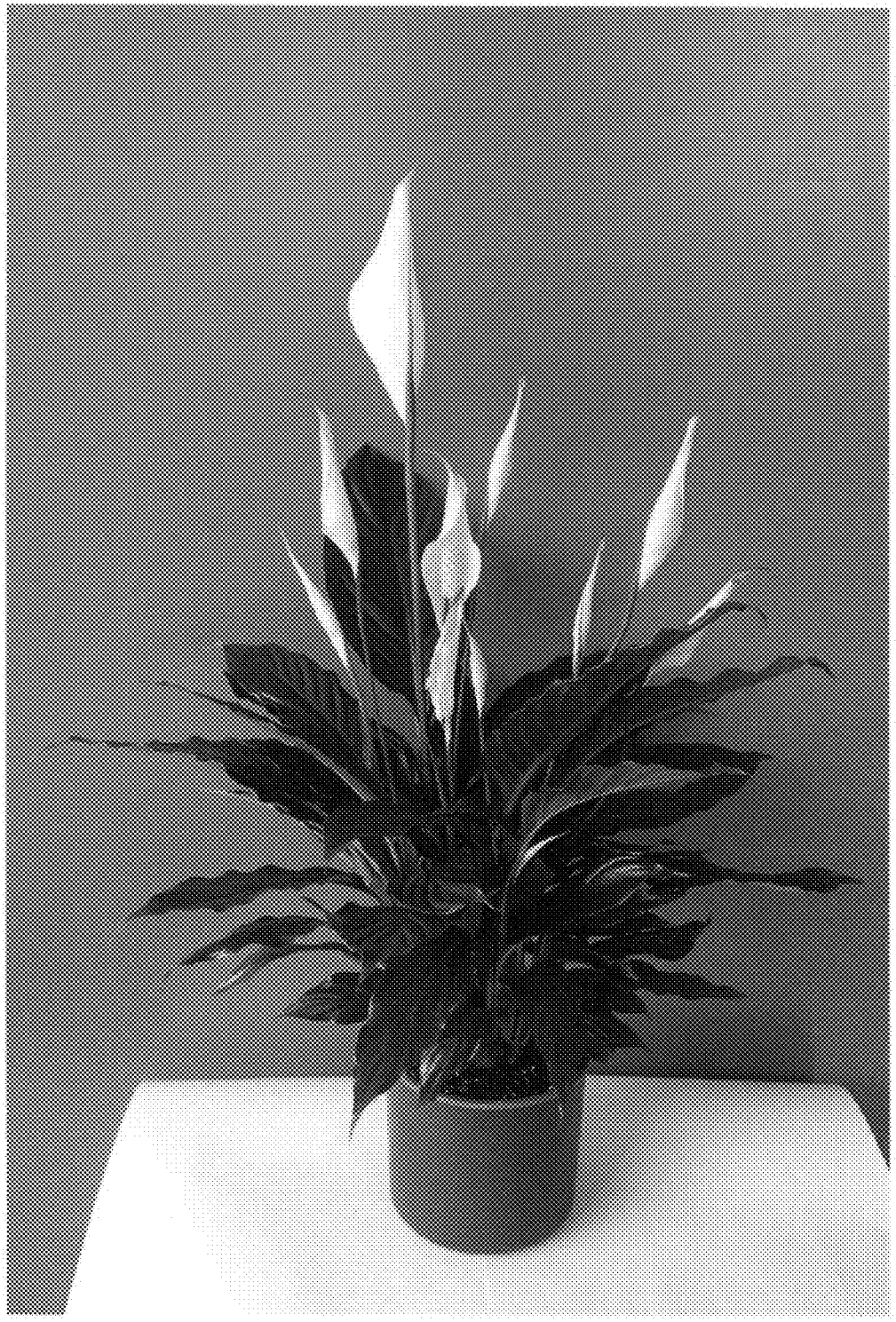

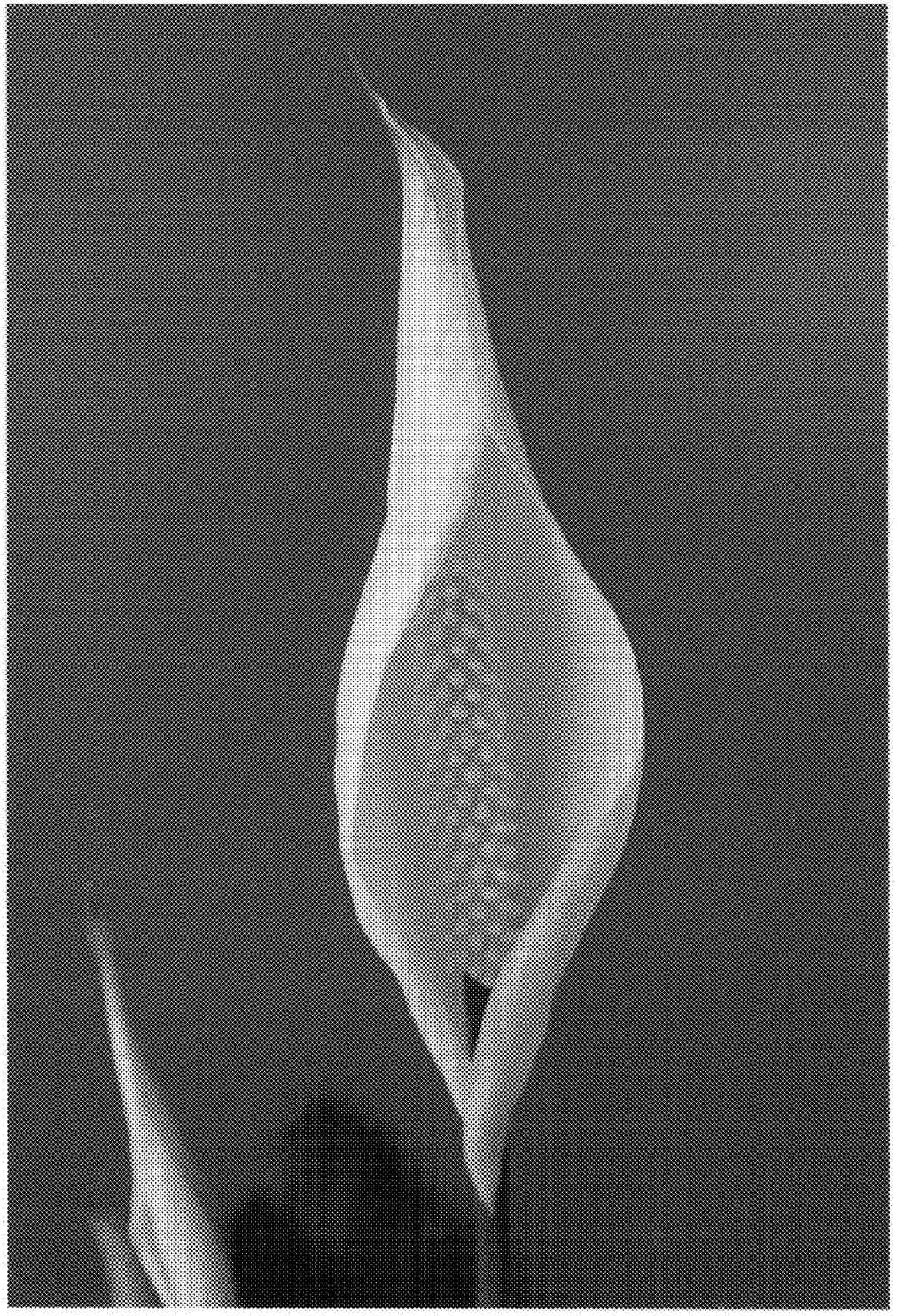

* * * * *